United States Patent [19]
Lee

[11] Patent Number: 5,619,993
[45] Date of Patent: Apr. 15, 1997

[54] METHOD OF CONTROLLING CURVATURE OF A MEDICAL DEVICE

[76] Inventor: Haojun Lee, The First People's Hospital of Shaoguan City 33 Dongti Rd., Shaoguan City, Guangdong, China

[21] Appl. No.: 402,319

[22] Filed: Mar. 10, 1995

Related U.S. Application Data

[63] Continuation of Ser. No. 126,749, Sep. 27, 1993, abandoned, which is a continuation of Ser. No. 798,549, Nov. 26, 1991, abandoned.

[30] Foreign Application Priority Data

Nov. 30, 1990 [CN] China .................................. 901094811

[51] Int. Cl.$^6$ .............................................. A61M 25/092
[52] U.S. Cl. ............................ 128/642; 604/49; 604/95; 600/146
[58] Field of Search ................................ 604/95, 96, 49; 606/194, 192, 157, 198; 128/772, 642; 600/116, 115, 146

[56] References Cited

U.S. PATENT DOCUMENTS

| | | | |
|---|---|---|---|
| 3,665,928 | 5/1972 | Del Guercio | 604/95 |
| 4,685,473 | 8/1987 | Karcher et al. | 128/774 X |
| 4,906,230 | 3/1990 | Maloney et al. | 604/95 |
| 4,920,980 | 5/1990 | Jackowski . | |
| 4,983,165 | 1/1991 | Loiterman | 604/95 |
| 4,984,564 | 1/1991 | Yuen | 128/20 |
| 5,308,323 | 5/1994 | Sogawa et al. | 604/95 |

OTHER PUBLICATIONS

Cardiac Catheter for Examination and Diagnosis pp. 187–190, first edition of Feb. 1979.
Yu Quinan et al., Medical Optical Instruments, first edition in Mar. 1988, pp. 364–369.

*Primary Examiner*—Michael H. Thaler
*Attorney, Agent, or Firm*—Ian C. McLeod; Mary M. Moyne

[57] ABSTRACT

The medical soft equipment and its means and instruments for controlling curvature relates to a piece of curvature controlling equipment of the kind which includes a pressure source, a pressure control unit as well as a soft tube (1) with one or more pressure control cavity or cavities (2) positioned inside, which is conductive to fluid pressure-transmitting medium. By using the pressure source, the pressure control unit, a kind of fluid pressure-transmitting medium and the soft tube with the pressure control cavity or cavities, differential pressures inside the cavity can be used to control the curvature of the needed part of the medical soft equipment, thus accomplishing the object of the present invention, which possesses the such merits as taking little space, alleviating the patient's suffering during operation with less serious tissue injuries, safe and reliable to manipulate, easy to control, and facilitating batch production.

3 Claims, 5 Drawing Sheets

$P_2$
$(P_2 > P_1)$

METHOD OF CONTROLLING CURVATURE OF A MEDICAL DEVICE

This is a continuation of application Ser. No. 08/126,749 filed on Sep. 27, 1993, now abandoned, which is a continuation of Ser. No. 07/798,549, filed Nov. 26, 1991, now abandoned.

This invention relates to a kind of medical soft equipment and its means and instruments for controlling curvature, which belong respectively to an artificial organ (a prothesis) or a piece of medical equipment, its controlling instruments as well as its uses in the biomedical engineering. In order to maintain people's health, we have to make use of various kinds of medical equipment, such as inserting or planting by every possible means the artificial organ or other medical equipment into various kinds of organs, tissures or cavities inside the body to make diagnosis, to give treatment, to perform surgical operations or to serve as an artificial replacement to restore physiological functions. However, as the inserting (or planting) passage or the surgical incision always seems too small, the shape of the curved organ, the tissure or the body cavity too narrow, and the curvature of the curved organ, the tissure or the body cavity at each position changing too often, in order to make the insertion or plantation less harmless, to minimize tissue injuries and to increase the efficiency and success rate, the curvature of the equipment for inserting or planting must be controlled at certain position or direction to be adapted to the the shape of the curved organ, the tissure or the body cavity at each position. In prior art, solutions generally adopted are as follows:

1. by manufacturing the equipment into a preformed curve: However, rich experience and high techniques are needed in its application. For example, we usually make the front part of the angiographic catheter into a fixed curve. By the combined actions of rotating and pushing, the catheter could be inserted into the right ventricle. But if the curvature of the front part is not sufficient, the catheter shall not get into the right atrium. In this case, the curvature is increased often by pushing blindly the front part of the catheter against any position of the right atrium for some time or by pulling it out and curving the front part with fingers, as is stated in the Sones & Judkins' method in coronary arteriography (refer to "Cardiac Catheter for Examination and Diagnosis", p. 187–190, first edition of Feb. 1979, compiled by Mao Jiwen and Sun Ruilong of Fuwai Hospital of the Chinese Medical Academy). In Sones' method, a preformed and slightly curved catheter is applied and then, by pushing it at the root of the aorta to achieve certain curvature and searching repeatedly for the mouth of the coronary artery, inserted into the right place while in Judkins' method, two catheters with different curvatures are used to be inserted respectively into the right and left coronary arteries and then replaced. Such a method as making the equipment into a fixed curve is somewhat of blindness. It demands high operating technique and more time in the application and therefore is apt to entail pains and dangers upon the patients with tissue injury and other complications such as vascular thrombosis, embolism, hemorrhage, infection and severe arrythemia. As a result, the success rate is adversely affected.

2. by making the whole equipment or its front part with certain litheness upon which the insertion is applied: This method takes advantage of the inserting or pushing force to make the front part of the equipment against the side of the curved organ or body cavity, thus creating a radial moment to curve the front part and make it appliable to the curvature of the passage, as is practised nowadays in manufacturing the electrode of the artificial cochlea, the bedside micro-catheter as well as the guide wire at the front point of the PTCA balloon catheter. As the curvature of the equipment is effected by inserting and pushing blindly, the operation is very hard to control and unavoidably causing tissue injury, which could be particularly serious when the direction of the inserting or pushing forms a larger angle with the tissue side. As the application demands very skillful technique, it is time-consuming, difficult to be used widely, and unlikely to be successful. Clinical experiences show that inserting the electrode of the artificial cochlea into the fragile and delicate cochlear scala tympani often leads to the laceration of the spiral ligamenta, the fracture of the osseous spiral lamina and the perforation of the basilar membrance, and subsequently gives rise to the fibrosis of the cochlea tissue, the formation of the new bone as well as the acoustic neurve degeneration. Moreover, a cardic catheter with excessive litheness is often short of axial rigidity, thus making the pushing difficult or even forming a knot in the heart. The insertion of the PTCA balloon catheter often brings about further injuries to the endarterium of the coronary artery, thus leading to the new postoperative stenosis and obstruction or even to the perforation of the coronary artery which would endanger the patient's life.

3. by inserting a guide wire into the inner longitudinal cavity of the equipment: By changing the curvature of the guide wire properly, the curvature in certain section of the equipment could be changed, as is done in the commonly used angiocardiographic catheter, the pigtail catheter, the silastic pace-making catheter, the PTCA balloon catheter as well as the Tip-controllable catheter disclosed in the U.S. Pat. No. 4,920,980, 1990. In the practical application, the curvature of the guide wire is often achieved by curving with hand and therefore difficult to have an accurate control. Once the guide wire gets into the body, its curvature is fixed. To change the curvature, the guide wire has to be extracted or replaced. Therefore, an operation like this is very difficult and time-consuming and likely to cause hemorrhage, thrombosis, infection or even the breakage of the guide wire inside the body, which would demand a surgical operation to pull it out, thus increasing the suffering and danger to the patient.

4. by using a steel wire-"snake-bone links" mechanism to control the curvature of the equipment (refer to "Medical Optical Instruments", first edition in Mar. 1988, compiled by Yu Qinan et al., p.364–369, "The Curvature Control of the Endoscope"). This method has been used in controlling the curvature of the endcoscope for years and is now reaching perfection. Its fundamental principle is by pulling a number of steel wires attached to the links of the mechanism to curve certain part of the equipment. As the curvature is controlled by the wires, the mechanism is complicated and bulky and difficult to be made into a small diameter pipe, thus limiting its application. In addition, if an excessive force is applied in pulling the wires, it shall damage the mechanism or even break the optical fibre, thus affecting the service life of the equipment. Furthermore, a pipe with larger diameter shall increase the difficulty in inserting and the suffering of the patient.

It is the object of the present invention to solve the problems remained in the prior art and to provide a piece of very reliable medical soft equipment and its means and instruments for controlling curvature. As the present invention is simple in structure and easy to operate, its diagnostic and therapeutic efficiency shall be favorably increased. As the curvature of the equipment can be easily controlled, it alleviates the patient's suffering with less serious complications such as tissue injury, hemorrhage, thromboembolism, arrythemia or even sudden death.

The object of the present invention can be accomplished in the following steps:

A kind of medical soft equipment is described, characterized in that inside the soft tube 1A of the medical soft equipment as shown in the accompanying drawings is at least one pressure control cavity 2A—an inner longitudinal cavity with either the distal or tip end sealed and its mouth connected to the pressure source, and between the curvature in the needed part of the medical soft equipment and the pressure inside the pressure control cavity 2A there exists a specific functional relationship. The medical soft equipment is preferably characterized in that said soft tube 1A is a kind of thin-walled, hollow angle pipe or spiral tube with one end sealed and an oblate or oval cross section, and its hollow cavity can be used as pressure control cavity 2A, or as both pressure control cavity 2A and function cavity, and when the inside of the pressure control cavity 2A is in a state of being pressed, the soft tube 1A is tending to have a round cross section, and a tractive stress appears along the outer edge of the bending part of the soft tube 1A and along the inner edge an expansion stress occurs, and with the increase of the pressure, the soft tube 1A is tending to stretch straight out. The medical soft equipment is further preferably characterized in that said soft tube 1A is a one-end-sealed soft tube with at least one eccentric pressure control cavity 2A and a central function cavity 3A, and when the pressure control cavity 2A is in a state of being pressed, the soft tube 1A is tending to be straightened. The medical soft equipment is still further characterized in that in said soft tube 1C, there are installed two or more pressure control cavities 2C, which are separated by a neutral or separating layer between them, and when the pressure inside the pressure control cavities is in an unbalanced state, the soft tube 1C shall curve to the side of lower pressure.

In order to change the curvature of the medical soft equipment, a kind of fluid shall be adopted as a sort of pressure-transmitting medium and conducted into at least one pressure control cavity of the specially designed equipment. By changing the pressure of the fluid, the pressure inside the equipment can be changed and the curvature changes at certain part or several parts of the medical soft equipment can be controlled according to the shape of the curved organ or body cavity, thus securing a safe and reliable outside control over the inside diagnosis and therapy when the medical soft equipment gets into the body. Inside the soft tube (1) of the medical soft equipment as shown in the accompanying drawings is at least one pressure control cavity (2)—an inner longitudinal cavity with either the distal or tip sealed and its mouth connected to the pressure source. Between the curvature in the needed part of the medical soft equipment and the pressure inside the pressure control cavity (2) there exists a specific functional relationship, through which the medical soft equipment can be properly adjucted to the right curvature as is needed by the curved organ or body cavity and reduce the pain to the patient and the complications as well as such as tissue injury, hemorrhage, thrombiembolism, arrhythemia and sudden death, thus increasing the reliability and success rate of the operation. As this kind of medical soft equipment control is the curvature through the fluid medium conducted into the pressure control cavity, it can be used for various kinds of medical soft equipment that demands a control of its curvature, such as artificial cochlea and artificial joints, etc. The method of controlling the curvature of the medical soft equipment in the present invention is carried out by using a pressure source, a pressure control device, a kind of fluid pressure-transmitting medium and a piece of medical soft equipment with at least one pressure control cavity (2), the inner pressure of which can be used to change the curvature of the equipment and controlled by the specific functional relationship between the curvature in the needed part of the medical soft equipment and the pressure inside the pressure control cavity (2), thus making the curvature suit each position in the course that the medical soft equipment is inserted into the body. As this method of controlling is safe and reliable, easy to operate and to control, and therefore good for achieving better diagnostic and therapeutic results. Either a gas, a liquid or a gel-type substance shall be adopted as a pressure-transmitting medium, depending on the safety, the reliability as well as the need in the practical application.

The curvature-controlling devices of said medical soft equipment in the present invention include a pressure source and other pressure-controlling devices, among which, a. the pressure source can be either a forcing pump, a spring plunger or any other pressure-generating instruments;

b. the pressure-controlling devices can be either a pressure-adjusting valve, a spring adjuster or a fluidic control system.

The intensity and adjusting range of the pressure depends on the needs of the medical soft equipment in use. As for the medical soft equipment with an endoscope, its air-supplied and water-supplied pumping system can be used as the pressure source.

The object of the present invention can also be accomplished in the following steps:

The soft tube 1A of the medical soft equipment as shown in FIGS. 1, 2, 3 and 4 is a kind of thin-walled, hollow angle pipe or spiral tube with one end sealed and a oblate or oval cross section. Its hollow cavity can be used as pressure control cavity 2A, or as both pressure control cavity 2A and function cavity. When the inside of the press control cavity 2A is in a state of being pressed, the soft tube 1A is tending to have a round cross section, and a tractive stress appears along the outer edge of the bending part of the soft tube 1A and along the inner edge an expansion stress results. With the increase of the pressure, the soft tube 1A is tending to stretch straight out. This method in controlling the curvature of the medical soft equipment can be used in the light of the Bourdon Tube Principle to exercise control over the pressure inside the pressure control cavity and the curvature in the needed part of the medical soft equipment in accordance with the following function relationship:

$$\Delta\alpha = K \frac{\alpha p}{E} f(A, B, t, R)$$

In the formula $\Delta\alpha$ stands for the point turning angle; K, empirical constant determined by a certain number of model tests; E, the elastic modulus of the material; $\alpha$, the bending angle of the whole medical soft equipment; p, the pressure difference between the inner and the outer side of the pressure control cavity; A and B stand respectively for the length of the major and the minor axis of the cross section; t, the thickness of the wall; R, the bending radius. In practical application, the shape of the cross section is determined by the real need, the requirement of the material and the size of the equipment.

The medical soft equipment of the present invention as shown in FIG. I, 2, 3 and 4 is the embodiment of a curvature-controllable artificial cochlea electrode designed according to the above-mentioned principle. The soft tube 1A that constitutes the electrode is a hollow spiral tube with an oblate cross section and one end sealed. The controlling of its curvature is realized by adjusting the pressure of the inner cavity, namely, the pressure control cavity 2A. Before the artificial cochlea electrode being inserted into the scala tympani, the shape of its cross section is tending to be round and the tube straightened. At this moment, along either the major or the minor axis there exists sufficient rigidity that helps to guide the direction and insertion. When it gets into certain depth, by releasing the pressure inside the cavity (2A) gradually, the tube shall become curved by degrees. If, in the entire process of insertion, an appropriate pressure controlling is exercised in making the electrode adapted to the curvature of the scala tympani as it is inserted into different depth, the tissue injury of the scala tympani made by the electrode can be reduced. By selecting the material and the sizes (A, B, t, R) properly, the mechanical requirement mentioned above can be easily met in controlling the curvature of the electrode by adjusting pressure.

The object of the present invention can be accomplished by the following steps as well:

The soft tube 1A of the medical soft equipment as shown in FIG. 5, 6, 7 and 8 is a one-end-sealed soft tube with an eccentric pressure control cavity 2B and a central function cavity 3B. When the pressure control cavity 2B is in a state of being pressed, the soft tube 1A is tending to be straightened. In the light of the principle as is shown in FIG. 9, 10, 11 and 12, when a pressure P is exerted inside the pressure control cavity 2B, an equivalent stress N=pF shall occur inside its normal plane (cross section area F). The equivalent stress shall, through the center of the soft tube 1A, gain a bending moment M=Ne (e refers to eccentricity), which shall make the soft tube 1A being straightened. This method of controlling the curvature of the medical soft equipment is carried out by controlling the pressure inside the pressure control cavity 2B and the curvature in the needed part of the medical soft equipment in accordance with the following functional relationship:

$$\Delta\alpha = K \frac{\alpha p}{E} \left( \frac{e}{R_o - R} - 1 \right)$$

In the formula, $\Delta\alpha$ stands for the terminal turning angle; K, empirical constant determined by a certain number of model tests; E, the elastic modulus of the material; $\alpha$, the bending angle of the whole medical soft equipment; P, the pressure difference between the inner and the outer side of the pressure control cavity; e, the eccentricity of the pressure control cavity; R, the curvature radius of the curve formed by connecting the central points of the cross sections; R, the curvature radius of the neutral layer or the separating layer. In practical application, if the cross section of the eccentric pressure control cavity is in a fully round shape, its soft tube 1B needs higher controlling pressure to make itself straightened up than any other soft tube with either an oblate or oval cross section. Moreover, the round cross section takes more inner space of the medical soft equipment. Therefore, a combined application of the two above-mentioned methods shall reduce the controlling pressure and save the inner space of the equipemnt, thus bringing the advantages of the two into full display.

The medical soft equipment as shown in figures from 5–16 are the embodiments of a kind of coronary arteriographic catheter designed through the combined application. Said medical soft equipment, before its pressure control cavity 2B is exerted with a pressure, is similar to Judkins' left coronary arteriographic catheter (as shown in FIG. 5). In each position of either "B—B" or "C—C", there is a curved part, the cross sections of which are shown a FIG. 6, 7 and 8. In addition to the original cavity, namely, the function cavity 3B, there is also a pressure control cavity molded or formed at its flank. As "A—A" is in the normal position, no curvature or curvature controlling there is needed and, therefore, the cross section of the pressure control cavity 2B at "A—A" is in small circle. When being put pressure on, only its axial regidity is increased,thus facilitating the inserting, the pushing as well as the rotating. As the cross section of the pressure control cavity at "B—B" is oblate in shape and the ratio of its major axis to the minor axis is high, it is very sensitive to the controlled pressure and liable to be straightened at the bending part. As the cross section of the pressure control cavity 2B at "C—C" is also oblate in shape but the ratio of its major axis to the minor axis is lower than that at the position of "B—B", it wants higher controlled pressure to be stretched up. The highest pressure is needed at the beginning of the insertion as it is easy to insert or push when the whole soft tube 1B is straightened and the axial rigidity is increased. When it reaches the arcus aortae, the pressure shall be redused properly, thus restoring, first of all, the curve at the position of "C—C" while, at the position of "B—B", it is still kept straight under the pressure as it has a higher ratio of the major axis to the minor axis at the cross section of the pressure control cavity 2B. At this moment, the tube of the medical soft equipment appears as Judkins' right coronary arteriographic catheter and therefore is easy to get through the arcus aortae and to be inserted into the right coronary artery. when it is in , the pressure shall be fully reduced to restore the function cavity (3B) to its normal size, thus facilitatint the passing through of the radiographol. This method can also be applied in controlling the coronary balloon dilatation catheter to get into the narrow place by making use of the curvature of its front part. As the right coronary arteriography or the balloon dilatation is accomplished, the front part shall be withdraw to the root of the aorta. As the pressure is fully reduced and the curvature at the positions of "B—B" and "C—C" is fully restored, its shape is now similar to Judkins' left coronary arteriographic catheter, and thus the left coronary arteriography or balloon dilatation can be carried out in accordance with Judkins' method without the necessity of changing the medical soft equipment. Since the whole process is accomplished by changing the curvature of the medical soft equipment through the adjustment of the pressure and no replacement for the medical soft equipment is necessary, the method is therefore in possession of not only the advantages of the Sones' method in having less chance of suffering the complications such as hemorrhage and affection but also those of the Judkins' method as being easy to learn and to operate.

The medical soft equipment and its means for controlling curvature of the present invention can be equally used for such catheters as pediatric cardiac catheters, PTCA balloon catheters, various kinds of dextrocardiac catheters and pacemaking catheters, renal arteriographic catheters, hepatic catheters used in intervenient therapy as well as catheters used in other vessels or body cavities in order to have an easier and safer operation, to reduce the pain and danger to the patient as well as to heighten the success rate and the curative effect.

The object of the present invention can also accomplished in the following steps: The soft tube 1C of the medical soft equipment as shown in FIG. 17 can be the bellows with separate the pressure cavities. In said soft tube 1C, there are installed two or more pressure control cavities 2C, separated by a neutral or separating layer between them. When the pressure inside the pressure control cavities is in an unbalanced state, the soft tube 1C shall curve to the side of lower pressure. Based on the principle that the end displacement occurs while the pressure inside the bellows is changing, two or more pressure control cavities 2C are uniquely designed with their inner part separated from each other. By adjusting the pressure difference between the pressure control cavities, end displacement shall occur by degree and in different directions, thus resulting in a bending moment, and the curvature of the soft tube 1C of the medical soft equipment can be controlled by adjusting the pressure. For such ordinary medical soft equipment as bellows with their pressure cavities separated, the control of the pressure inside its pressure control cavities 2C and the curvature in the needed part of the medical soft equipment can be realized in accordance with the following function relationship:

$$W = K \frac{np}{E} f(R_0, R_1, r_c, t, \beta)$$

In the formula, W stands for distal displacement; K, empirical constant determined by a certain number of model tests; p, the pressure difference between the inner and the outer side of the pressure control cavity; E, the elastic modulus of the material; n, the ripple value; $R_0$, the convex curvature radius of the bellows; $R_1$, the concave curvature radius of the bellows; $r_0$, the radius of the ripple arc; t, the thickness of the wall; $\beta$, the compact-angle.

The distal displacement of the medical soft equipment under pressure depends on the elastic modulus and geometrical size of the material. It is in direct proportion to pressure p and ripple value n and in reverse proportion to the cube of the thickness of the wall and to the square of $R_0/R_1$, the ratio of the convex curvature radius to the concave curvature radius.

In the light of this principle, the bellows can be separated into two or more pressure control cavities. The medical soft equipment shown in FIG. 17 of the present invention is the embodiment of an endoscope made of such bellows as having two separated pressure control cavities designed according to the above-mentioned principle. On condition that the geometrical size and the elastic modulus of the material of the two pressure control cavities are the same, a distal displacement shall occur when a pressure p is exerted inside one of two pressure control cavities 2C. If a pressure $p_B = -p_A$ is exerted inside the other pressure control cavity, a distal displacement $W_B = -W_A$ shall occur. when the neutral or separating layer remains constant, the length $L_A$ at one the side of the outer edge of the pressure control cavity equals the original length $L_0 + W_A$, the length at the other side $L_B = L_0 + W_B = L_0 - W_A$, and therefore the difference between them is 2 $W_A$. As the neutral or separating layer 4C remains constant and the distal plane is an entity, one side of the outer edge of the pressure control cavity 2C is analogous to be under a tractive force and the other side, to be under a compressive stress and the tubular body of the soft tube 1C curves to the side with lower pressure. From the other point of view, the volume of the pressure control cavity at one side is, when under pressure, tending to be increased and the ripples along the axial direction are apt to be stretched, while the volume of the other side, when the pressure is reduced, is tending to be decreased and the ripples along the axial direction are apt to be contracted and the tubular body curves to the side where the pressure is reduced. In this fashion, the curvature-controlable medical soft equipment can be made. Take the endoscope for instance, the optical fiber bindies as well as the biopsy passage can all be molded or formed inside the neutral or separating layer 4C in the equipment receiving cavity 6C. By adjusting the pressure difference between the cavities 2C, the curvature of the soft tube (1C) of the medical soft equipment can be controlled. To control the curvature in this fashion, the medical soft equipment takes little space with less manipulation and more assurance of good performance. It is also simple in structure with no movable parts inside, and thus can work safely and enjoy a long service life.

The methods mentioned above in the present invention share the common principle. They are all through the adjustment of the pressure inside the cavity to control the curvature of the medical soft equipment and therefore can be used in combination, especially when the equipment is multifunctional, able to contain cavities for different functions and with a variation of their space and arrangement, such a combination of the above-mentioned methods seems to be more important to meet the wide demands for the application.

The invention will be further described with reference to the accompanying drawings, in which.

Figure 1:
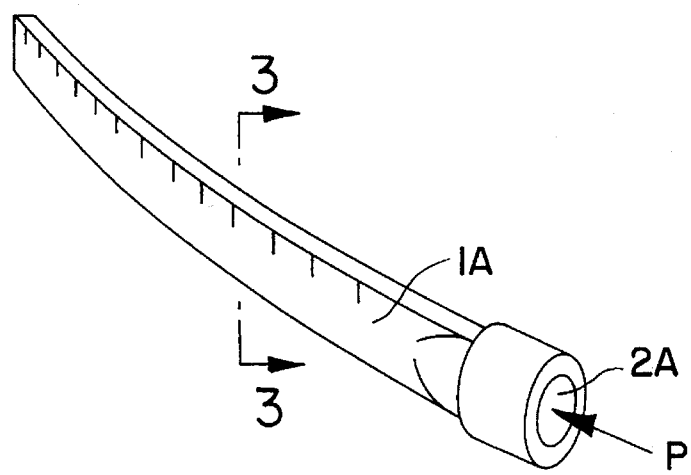
FIG. 1 is the schematic drawing of the electrode of the artificial cochlea made of the medical soft equipment of the present invention in its stretched state.
Figure 2:
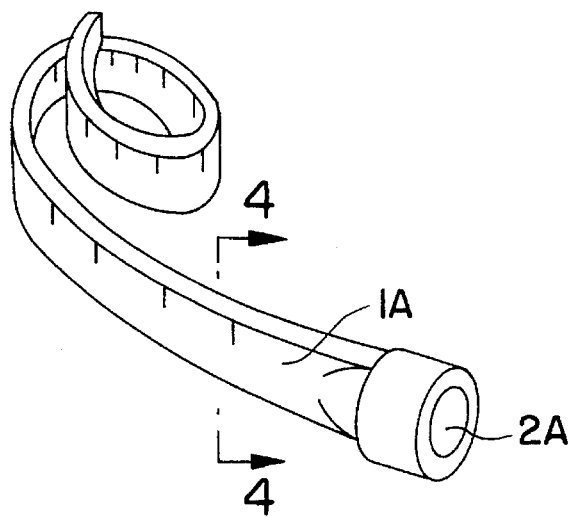
FIG. 2 is the schematic drawing of the electrode of the artificial cochlea made of the medical soft equipment of the present invention in its curved state.
Figure 3:
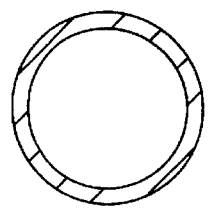
FIG. 3 is the enlarged section schematic drawing of "A—A" of FIG. 1.
Figure 4:
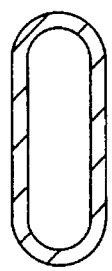
FIG. 4 is the enlarged section schematic drawing of "B—B" of FIG. 2.
Figure 6:
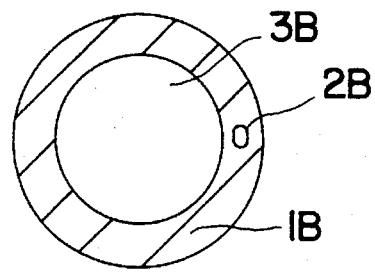
FIG. 6 is the enlarged section schematic drawing of "A—A" of FIG. 5.

The medical soft equipment of the present invention in FIG. 1, 2, 3 and 4 relates to the electrode of the artificial cochlea, the soft tube 1A of which contains a pressure control cavity 2A with oblate section, together with its various changes when under pressure control. The pressure control cavity can serve at the same time as the function cavity. Before the control cavity is brought under pressure in FIG. 2 and 4, it has an oblate section and looks like a spiral. When the control cavity is brought under pressure as shown as shown in FIG. 1 and 3, its section is getting round and the tubular body of the soft tube 1A of the electrode of the artificial cochlea is straightened. When the pressure inside the cavity is altered, the tubular body of the soft tube 1A will have different curvatures.

Figure 5:
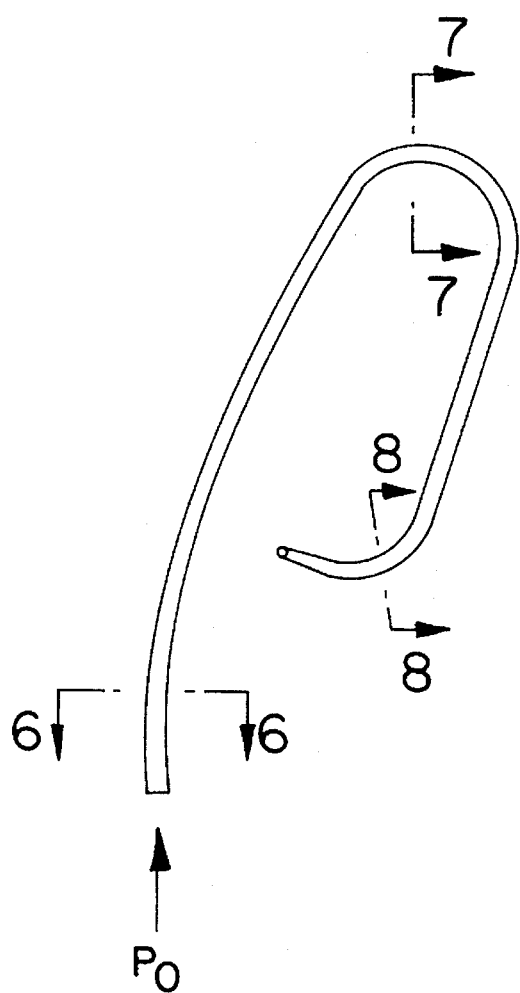
FIG. 5 is the schematic drawing of the coronary arteriographic catheter made of the medical soft equipment of the present invention in its curved state.
Figure 7:
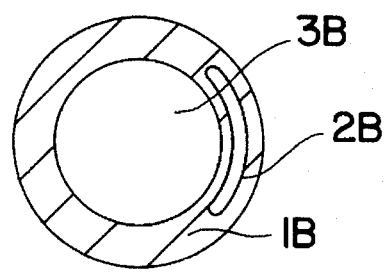
FIG. 7 is the enlarged section schematic drawing of "B—B" of FIG. 5.
Figure 8:
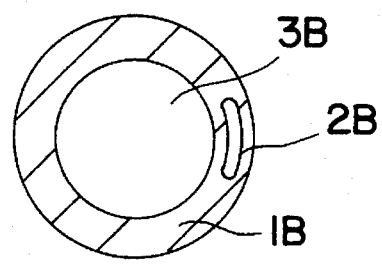
FIG. 8 is the enlarged section schematic drawing of "C—C" of FIG. 5.
Figure 10:
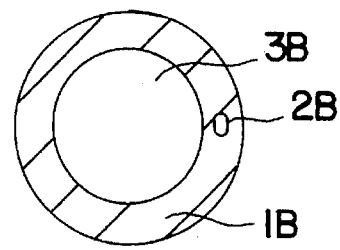
FIG. 10 is the enlarged section schematic drawing of "A—A" of FIG. 9.
Figure 9:
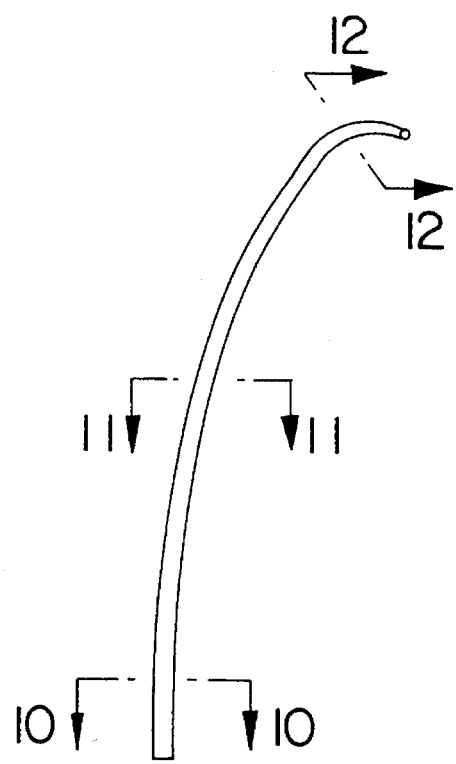
FIG. 9 is the schematic drawing of the coronary arteriographic catheter made of the medical soft equipment of FIG. 5 in its partially stretched state.
Figure 11:
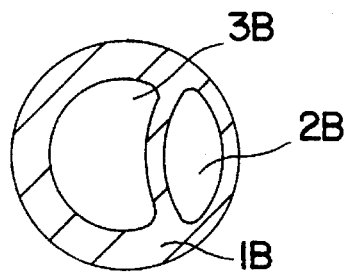
FIG. 11 is the enlarged section schematic drawing of "B—B" of FIG. 9.
Figure 12:
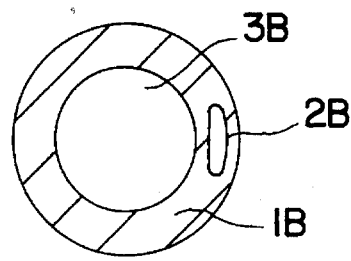
FIG. 12 is the enlarged section schematic drawing of "C—C" of FIG. 9.
Figure 14:
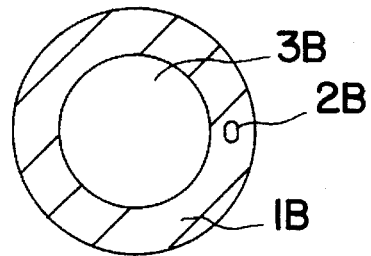
FIG. 14 is the enlarged section schematic drawing of "A—A" of FIG. 13.
Figure 15:
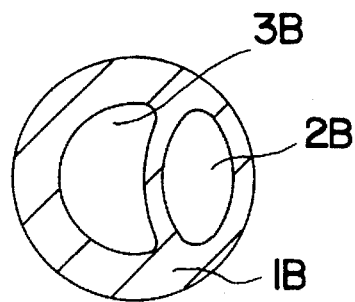
FIG. 15 is the enlarged section schematic drawing of "B—B" of FIG. 13.
Figure 13:
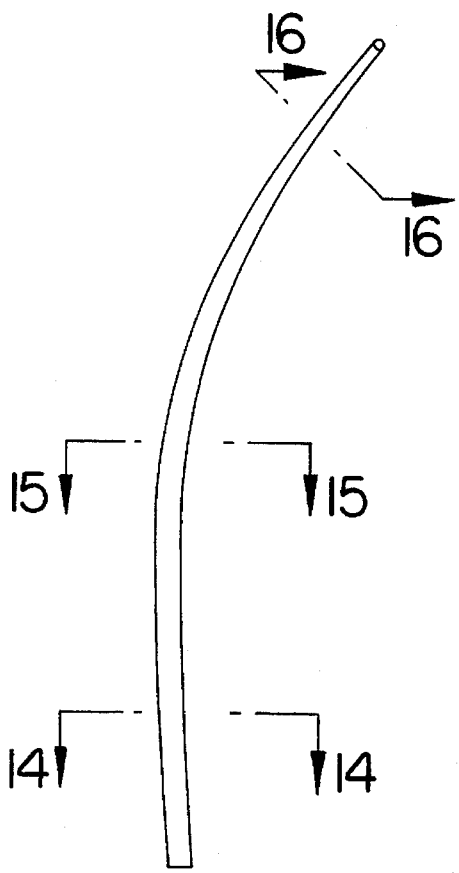
FIG. 13 is the schematic drawing of the coronary arteriographic catheter made of the medical soft equipment of FIG. 5 in its fully stretched state.
Figure 16:
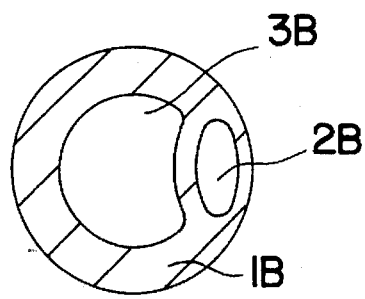
FIG. 16 is the enlarged section schematic drawing of "C—C" of FIG. 13.

The medical soft equipment of the present invention in FIG. 5–8, 9–12 and 13–16 relates to the coronary arteriographic catheter, the soft tube 1B of which contains an eccentric pressure control cavity 2B and a central function cavity 3B, together with its various changes when under pressure control. As the section "A—A" is in the normal segment of the soft tube and its pressure control cavity 2B is of smaller circle in shape, the section will remain basically the same when under different pressures. The section "B—B" is in the first bending segment and its pressure control cavity is oblate in shape. The section "C—C" is in the second bending segment and its pressure control cavity is also oblate, however its major axis and minor axis as well as their ratio are smaller than those of the section "B—B", thus demanding higher pressure, as compared with the section "A—A", to have a change of its shape and to straighten the second bending segment. The medical soft equipment shown in FIG. 5 is in the shape of Judkins' left coronary arteriographic catheter and can be used for left coronary arteriography before its pressure control cavity 2A is exerted with a pressure ($P_0=0$). When the pressure control cavity 2B is exerted with a pressure $P_1$, the external form and the section of the medical soft equipment of the present invention are as shown in FIG. 9, 10, 11 and 12. As the major axis of the pressure control cavity 2B of the section "B—B" in the first bending segment is longer than that of the section "C—C" in the second bending segment, the section "B—B" is easy to become round in shape under pressure $P_1$. As a result that the section "B—B" in the first bending segment is easy to be straightened while the section "C—C" in the second segment is still in a curved state, the medical soft equipment is similar to Judkin's right coronary arteriographic catheter and can be used for right coronary arteriography. When the pressure control cavity (2B) is exerted with a pressure $P_2$ ($P_2>P_1$), the external form and the section of the medical soft equipment are as shown in FIG. 13, 14, 15 and 16. The pressure control cavity 2B of the section "C—C" in the second bending segment is also tending to be round in shape under the pressure $P_2$, thus making this part into a stretched state. As the first bending segment is in a more stretched state, the whole medical soft equipment is basically stretched and, with sufficient axial rigidity, easy to be inserted in or pass through the aorta.

Figure 17:
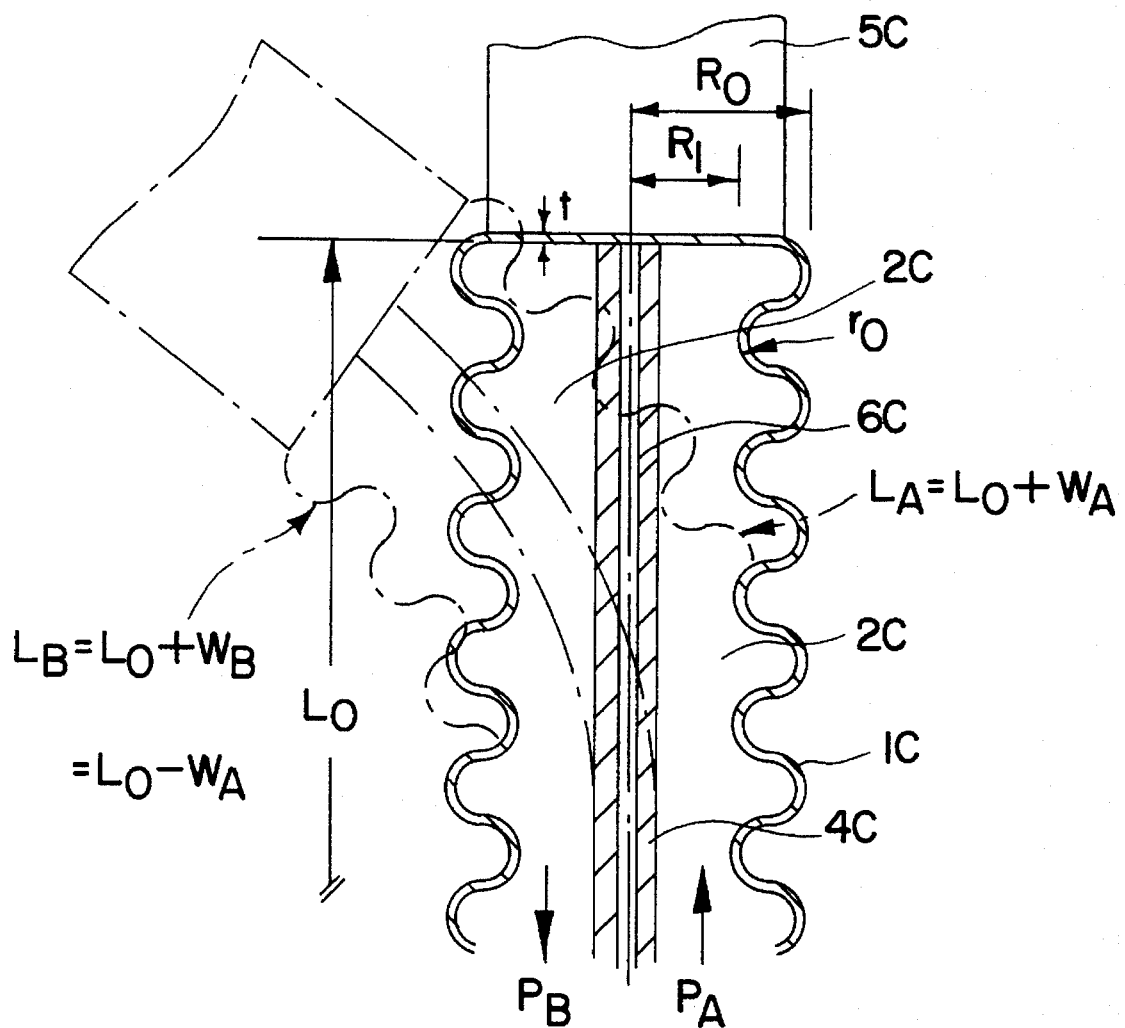
FIG. 17 is the schematic drawing of the endoscope made of the medical soft equipment of the present invention.

The medical soft equipment of the present invention in FIG.17 relates to an endoscope made of bellows, the soft tube 1C of which contains separated pressure control cavities 2C, together with its various changes when under pressure control. Inside its soft tube 1C there are two pressure control cavities 2C which are separated from each other by a neutral or separating layer 4C. Inside the neutral or separating layer, devices such as optical fiber bindles, air and flushing piples as well as biopsy passages can be installed in the equipment receiving cavity 6C. In the front part of the soft tube 1C, there is the body 5C of the endoscope. When the pressure control cavity 2C at one side is exerted with a positive pressure $P_A$, while the pressure control cavity 2C at the other side is exerted with a negative pressure $P_B$, the length $L_A$ at one side of the outer edge of the pressure control cavity (2) under the positive pressure $P_A$ extends from the original length $L_0$ to $L_0+W_A$, the length at the other side under the negative pressure P contracts from the original length $L_0$ to $L_0-W_B$. When $P_B=-P_A$, $W_B=-W_A$, $L_B=L_0+W_B=L_0-W_A=L_A-2W_A$. As the outer edges at the two side two sides are not in equal length, a radial bending moment occurs and thus makes the tubular body of the soft tube 1C curved as shown in the dotted lines.

The present invention, as compared with the prior art, possesses the following merits:

(1) The medical soft equipment takes little space. As its pressure source and pressure control devices are all extracorporeal, the size of the equipment to be inserted into the body is greatly reduced, thus miniaturizing the medical soft equipment of which the curvature needs to be controlled. To be more important, it is also possible to have curvature controlling for those pieces of medical soft equipment that were curvature-uncontrollable and used only with high operative skills, thus reducing the suffering of the patient with less serious complications such as tissure injury, hemorrhage, thrombiembolism, perforating organ, severe arrhythemia or even sudden death, and possessing distinct safety and reliability.

(2) The medical soft equipment is simple and reliable in structure. As only one or more pressure control cavity is added to the medical soft equipment in order to control the curvature of the needed part, as there is no movable components or complicated structure inside the medical soft equipment, there is no worry of damage or maintenance.

(3) The medical soft equipemnt is likely to find a wide application. As the pressure source and pressure controlling can be provided fully based on the existing technical condition, as the equipment is easy and flexible to operate, it demands no high skill from the manipulator.

(4) As the cost is not high, it facilitates batch production.

I claim:

1. A method for controlling curvature of a medical device which is used as a catheter as the medical device is inserted into the body of a patient which comprises controlling the curvature by using a pressure source, a pressure control unit connected to the source, a fluid pressure-transmitting medium and a pressure control cavity along the entire length of the medical device and containing the medium and connected to the source and unit, wherein the medical device is curved prior to the fluid pressure transmitting medium being supplied from the source and is straightened by the medium from the source, wherein the pressure control cavity has at least three parts with different cross-sections along the length of the medical device which are straightened at different pressures wherein the different parts curve to differing extents due to the different cross-sections allowing the medical device to have different curvatures at the different parts at a given pressure of the pressure transmitting medium and wherein the inner pressure of the cavity can be used to change the curvature of the medical device controlled by a specific functional relationship between the curvature in the medical device and the pressure inside the part of the pressure control cavity, thus making the curvature suit each position in the course that the medical device takes into the body.

2. The method of the medical device for controlling curvature according to claim 1, which comprises controlling the pressure inside the part of the pressure control cavity and the curvature in the medical device in accordance with the following functional relationship:

$$\Delta\alpha = K \frac{\alpha p}{E} \left( \frac{e}{R_o - R} - 1 \right)$$

wherein $\Delta\alpha$ stands for a terminal turning angle; K is an empirical constant determined by a certain number of model tests; E is an elastic modulus of the medical device; $\alpha$ is a bending angle of the whole medical device; p is a pressure difference between an inner and an outer side of the pressure control cavity; e is an eccentricity of the pressure control cavity; $R_o$ is a curvature radius of a curved formed by connecting central points of cross sections of the medical device and R is a curvature radius of a neutral layer or a separating layer in the cavity.

3. A method for controlling curvature of a medical device which is used as an electrode as the medical device is inserted into the body of a patient which comprises controlling the curvature by using a pressure source, a pressure control unit connected to the source, a fluid pressure-transmitting medium and a pressure control cavity along the entire length of the medical device, the pressure control cavity having different cross-sections along the entire length of the medical device and containing the medium and connected to the source and unit, wherein the medical device is angular with one end sealed and is spirally curved prior to the fluid pressure transmitting medium being supplied from the source and is straightened by the medium from the source, wherein control over the pressure inside the pressure control cavity and the different curvatures along the length of the medical device is implemented in accordance with the formula:

$$\Delta\alpha = K \frac{\alpha p}{E} f(A, B, t, R)$$

wherein $\Delta\alpha$ stands for a point turning angle; K is an empirical constant determined by a certain number of model tests; E is an elastic modulus of the medical device; $\alpha$ is a bending angle of the whole medical device; p is a pressure difference between an inner and an outer side of the pressure control cavity; A and B stand respectively for a length of a major and a minor axis of a cross section of the medical device; t is a thickness of the wall; and R is a bending radius wherein the medical device curves to differing extents along its length due to the different cross-sections allowing the medical device to have different curvatures along the length of the medical device at a given pressure of the pressure transmitting medium.

* * * * *

UNITED STATES PATENT AND TRADEMARK OFFICE
CERTIFICATE OF CORRECTION

PATENT NO. : 5,619,993
DATED : April 15, 1997
INVENTOR(S) : Haojun Lee

It is certified that error appears in the above-indentified patent and that said Letters Patent is hereby corrected as shown below:

Column 1, line 15, "tissures" should be --tissues--.

Column 1, line 21, "tissure" should be --tissue--.

Column 1, line 22, "tissure" should be --tissue--.

Column 1, line 24, "tissure" should be --tissue--.

Column 1, line 28, "tissure" should be --tissue--.

Column 2, line 1, "practised" should be --practiced--.

Column 2, line 18, "neurve" should be --nerve--.

Column 3, line 61, "thrombiembolism" should be --thromboembolism--.

Column 4, line 39, "press" should be --pressure--.

Column 4, line 67, "FIG. I, 2, 3 and 4" should be --FIG. 1, 2, 3 and 4--.

Column 5, line 23, "tube 1A" should be --tube 1B--.

Column 5, line 27, "tube 1A" should be --tube 1B--.

Column 5, line 32, "tube 1A" should be --tube 1B--.

Column 5, line 34, "tube 1A" should be --tube 1B--.

UNITED STATES PATENT AND TRADEMARK OFFICE
CERTIFICATE OF CORRECTION

PATENT NO. : 5,619,993
DATED : April 15, 1997
INVENTOR(S) : Haojun Lee

It is certified that error appears in the above-indentified patent and that said Letters Patent is hereby corrected as shown below:

Column 5, line 61, "equipement" should be --equipment--.

Column 6, line 3, "shown a FIG." should be --shown as FIG.--.

Column 6, line 10, "regidity" should be --rigidity--.

Column 6, line 23, "redused" should be --reduced--.

Column 6, line 33, "facilitatint" should be --facilitating--.

Column 6, line 38, "withdraw" should be --withdrawn--.

Column 6, line 51, "affection" should be --infection--.

Column 7, line 27, "bellows; $r_0$," should be --bellows; $r_c$,--.

Column 7, lines 48 and 49, "the length $L_A$ at one the side" should be --the length $L_A$ at one side--.

Column 7, line 65, "curvature-controlable" should be --curvature-controllable--.

Column 7, line 66, "bindles" should be --bundles--.

Column 9, line 27, "cavity 2A" should be --cavity 2B--.

Column 9, line 28, "($P_0$=0)" should be --($P_c$=0)--.

Column 9, line 58, "bindles" should be --bundles--.

UNITED STATES PATENT AND TRADEMARK OFFICE
CERTIFICATE OF CORRECTION

PATENT NO. : 5,619,993
DATED : April 15, 1997
INVENTOR(S) : Haojun Lee

It is certified that error appears in the above-indentified patent and that said Letters Patent is hereby corrected as shown below:

Column 9, line 59, "flushing piples" should be --flushing pipes--.

Column 9, line 66, "cavity (2)" should be --cavity (2C)--.

Column 10, line 3, "two side", first occurrence, should be deleted.

Column 10, line 19, "tissure" should be --tissue--.

Column 10, line 19, "thrombiembolism" should be --thromboembolism--.

Column 11, line 12 (Claim 2), "curved" should be --curve--.

Signed and Sealed this

Ninth Day of September, 1997

Attest:

BRUCE LEHMAN

Attesting Officer

Commissioner of Patents and Trademarks